United States Patent

Nakagawa et al.

[11] Patent Number: 6,026,690
[45] Date of Patent: Feb. 22, 2000

[54] VIBRATION SENSOR USING THE CAPACITANCE BETWEEN A SUBSTRATE AND A FLEXIBLE DIAPHRAGM

[75] Inventors: Yoshimori Nakagawa, Tokyo; Jun Kishigami, Saitama, both of Japan

[73] Assignee: Sony Corporation, Japan

[21] Appl. No.: 08/975,930

[22] Filed: Nov. 21, 1997

Related U.S. Application Data

[63] Continuation of application No. 08/592,397, filed as application No. PCT/JP95/01184, Jun. 14, 1995, abandoned.

[30] Foreign Application Priority Data

Jun. 20, 1994 [JP] Japan .................................. 6-137586

[51] Int. Cl.[7] ........................... G01H 11/08; G01P 15/12; G01P 15/125
[52] U.S. Cl. ...................... 73/654; 73/514.32; 73/514.34
[58] Field of Search .................. 073/514.16, 514.17, 073/514.18, 514.22, 514.23, 514.32, 514.34, 514.35, 514.36, 514.37, 514.38

[56] References Cited

U.S. PATENT DOCUMENTS

| | | | |
|---|---|---|---|
| 4,182,187 | 1/1980 | Hanson | 73/514.22 |
| 4,930,042 | 5/1990 | Wiegand et al. | 73/514.18 |
| 5,000,817 | 3/1991 | Aine | 73/514.18 |
| 5,008,774 | 4/1991 | Bullis et al. | 73/514.32 |
| 5,115,291 | 5/1992 | Stokes | 73/514.18 |
| 5,226,325 | 7/1993 | Komurasaki | 73/514.34 |
| 5,798,460 | 8/1998 | Nakagawa | 73/514.34 |

FOREIGN PATENT DOCUMENTS

| | | |
|---|---|---|
| 59-79700 | 5/1984 | Japan . |
| 63-15125 | 1/1988 | Japan . |
| 3137688 | 6/1991 | Japan . |
| 4158226 | 6/1992 | Japan . |
| 5164565 | 6/1993 | Japan . |

*Primary Examiner*—Hezron Williams
*Assistant Examiner*—Helen C. Kwok
*Attorney, Agent, or Firm*—Rader, Fishman & Grauer; Ronald P. Kananen

[57] ABSTRACT

A vibration sensor includes a substrate (7), a plate-like diaphragm (3) forming a capacitor, and holding assembly (2), (4), (6) for holding the diaphragm so as to be movable in parallel to the substrate. The diaphragm includes a plurality of flexible displacement portions (3c), (3d) for enabling the supporting portion of the diaphragm to be movable in parallel to the substrate. When vibrations are applied to the vibration sensor, the diaphragm portion of the diaphragm is vibrated and electrostatic capacity formed between the substrate and the diaphragm is changed based on the vibrations. Vibrations are detected on the basis of the change of electrostatic capacity. Since the vibration sensor includes the flexible displacement portions, the diaphragm becomes difficult to be vibrated due to a sound pressure and a vibration detected output can be prevented from being disturbed by the sound pressure.

9 Claims, 6 Drawing Sheets

VIBRATION SENSOR USING THE CAPACITANCE BETWEEN A SUBSTRATE AND A FLEXIBLE DIAPHRAGM

This application is a continuation of application Ser. No. 08/592,397 filed Feb. 1, 1996, now abandoned, which is a 371 of PCT Appln. No. PCT/JP95/01184, filed Jun. 14, 1995.

TECHNICAL FIELD

The present invention relates to a vibration sensor and a navigation apparatus. More particularly, this invention relates to a vibration sensor for detecting vibrations based on a change of electrostatic capacity and a navigation apparatus using such a vibration sensor.

BACKGROUND ART

Heretofore, there have been developed vibration sensors using an electret film. As shown in FIG. 1, a vibration sensor includes a closed case 30 containing a back plate 31 with an electret film formed thereon. A diaphragm 32 opposed to the electret film of the back plate 31 is disposed with a very small clearance between it and the back plate. The back plate 31 is fixed within the case 30. Electric charges are accumulated between the electret film of the back plate 31 and the diaphragm 32. In this case, the diaphragm 32 is formed of a thin metal plate and is supported so as to be easily vibrated. In principle, the vibration sensor shown in FIG. 1 senses how much electric field changes when the diaphragm 32 is vibrated. The result is a voltage signal that indicates an amount of vibrations applied to the sensor.

Specifically, if the diaphragm 32 is fixed, then the vibration sensor is vibrated together with a monitored object to which the vibration sensor is attached. When the vibration sensor is vibrated together with the monitored object, the back plate 31 is vibrated relative to the diaphragm 32. As a result, the electrostatic capacity between the back plate 31 and the diaphragm 32 is changed based on vibrations of the back plate 31. The detected change of the electrostatic capacity is output by the vibration sensor. Although it is considered that the diaphragm 32 is fixed, if the vibration sensor is fixed together with the detected object, then it is natural that the diaphragm 32 should be vibrated based on vibrations applied to the vibration sensor. In any event, the vibration sensor detects vibrations applied to the monitored object from the outside or vibrations generated in the monitored object as the change of electrostatic capacity accumulated between the diaphragm 32 and the back plate.

The back plate 31 and the diaphragm 32 are accommodated within the closed case 30 in order to prevent the diaphragm 32 from being vibrated by a sound pressure based on sounds applied to the vibration sensor from the outside so that the vibration sensor is able to detect only vibrations accurately. Specifically, if the diaphragm 32 is vibrated in response to sounds applied to the sensor, then the vibration sensor registers vibrations together with sound and the output from the vibration sensor contains an error component. In order to prevent this defect, the back plate and the diaphragm should be almost completely enclosed by the case 30. FIG. 2 is a graph showing a sound pressure frequency characteristic of the closed type vibration sensor. Since the case 30 is of the closed type, the vibration sensor responds to only a sound or sound pressure having a relatively low frequency and is unable to respond to a sound or sound pressure having a frequency higher than a certain frequency. When the vibration sensor is applied to a navigation apparatus in a vehicle, the vibration sensor tends to detect sounds generated in the vehicle, e.g., an automobile. There are then the problems that a position on a correct map cannot be displayed and that a correct position cannot be displayed on a map due to the error component from the vibration sensor.

Study of characteristics shown in FIG. 2 reveals that the sensor inevitably responds to the sound pressure of low frequency sounds applied to the vibration sensor and generates an erroneous output. For this reason, it is proposed to form a through-hole on the diaphragm. Specifically, when a response of the diaphragm relative to a sound pressure is in the state shown by the solid line in FIG. 3, if a through-hole is defined at the central portion of the diaphragm, then a minimum frequency response to sound pressure can be shifted to a higher frequency as shown by the broken line in FIG. 3. The minimum frequency response to sound pressure can be further shifted to a higher frequency as an area of the through-hole increases.

If the minimum frequency response to the sound pressure generated based on sounds applied to the diaphragm from the outside is raised by using a through-hole as described above, as shown in FIG. 2, then the diaphragm responds to only a sound pressure having a frequency higher than a band responsive to the sound pressure of the low frequency shown by the sound pressure frequency characteristic of the closed-type vibration sensor. As a result, the diaphragm responds only to vibrations applied to the sensor and the sensor can indicate those vibrations by the output signal.

If however the through-hole is defined at the central portion of the diaphragm to lower sensitivity to sound pressure with a low band frequency, there is then the disadvantage that the detection sensitivity of the vibration sensor is lowered. Specifically, the level at which the diaphragm without a through-hole detects vibrations shown by the solid line in FIG. 4. Then when the through-hole is provided in order to lower sensitivity to sound pressure of the low frequency, the output level of the detection signal is lowered as shown by the broken line in FIG. 4. The output level is lowered much more as the area of the through-hole is increased. That is, the through-hole decreases an area in which the diaphragm and the back plate oppose each other, lessening a usability of electric charges of the electret film. As a result, the output level of the detection signal is lowered.

Therefore, this kind of conventional vibration sensor cannot raise a vibration detection sensitivity to a desirable extent.

DISCLOSURE OF THE INVENTION

In view of the aforesaid problem, it is an object of the present invention to provide a vibration sensor with a satisfactory characteristic capable of detecting only vibrations with a high sensitivity and a navigation apparatus using such vibration sensor.

According to a first embodiment, a vibration sensor comprises a substrate, a plate-like diaphragm including a diaphragm portion, a supporting portion and a plurality of flexible displacement portions for coupling the diaphragm portion and the supporting portion such that the diaphragm portion and the supporting portion become able to move in parallel to the substrate, the plate-like diaphragm being opposed to the substrate with a predetermined interval and being disposed in parallel to the substrate to form a capacitor, and holding means for holding the substrate and holding the supporting portion of the diaphragm in such a manner that the diaphragm portion comes close to or away from the substrate in a parallel direction, wherein a vibration is converted into a change of electrostatic capacity formed between the diaphragm and the substrate and output as a detected output. With this arrangement, when the diaphragm is vibrated by vibrations applied to the vibration sensor, a detected electrostatic capacity is changed and therefore vibrations can be detected satisfactorily.

According to a second embodiment, in the vibration sensor according to the first invention, the plurality of flexible displacement portions are radiated from a center of the diaphragm portion. With this arrangement, the diaphragm can be vibrated satisfactorily and therefore vibrations can be detected satisfactorily.

According to a third embodiment, in the vibration sensor according to the second embodiment, the diaphragm includes between it and the plurality of flexible displacement portions means for canceling a sound pressure applied to the vibration sensor. With this arrangement, even when sounds are applied to the vibration sensor from the outside, the diaphragm can be prevented from being vibrated and therefore only vibrations applied to the vibration sensor can be detected.

According to a fourth embodiment, in the vibration sensor according to the third embodiment, the canceling means is composed of a plurality of opening portions disposed along a circumferential direction of the diaphragm portion disposed between the plurality of flexible displacement portions. With this arrangement, it is possible to satisfactorily cancel a sound pressure applied from the outside.

According to a fifth embodiment, in the vibration sensor according to the first embodiment, the holding means is a housing for accommodating therein the substrate and the diaphragm in substantially closed state and holding the substrate and the supporting portion of the diaphragm. With this arrangement, the inside of the sensor can be prevented from being smudged by dusts or the like. Moreover, the diaphragm can be prevented from being vibrated by a sound pressure based on sounds applied to the sensor. Thus, vibrations can be detected satisfactorily.

According to a sixth embodiment, a vibration sensor comprises a substrate, a plate-like diaphragm including a diaphragm portion, a supporting portion and a plurality of flexible displacement portions for coupling the diaphragm portion and the supporting portion such that the diaphragm portion and the supporting portion become able to move in parallel to the substrate, an electret film disposed either on the substrate at its surface opposing the diaphragm or on the diaphragm at its surface opposing the substrate, and holding means for holding the substrate and holding the supporting portion of the diaphragm in such a manner that the diaphragm portion comes close to or away from the substrate in parallel. With this arrangement, the diaphragm is vibrated by vibrations applied to the vibration sensor and thereby vibrations applied to the vibration sensor can be detected.

According to a seventh embodiment, in the vibration sensor according to the sixth embodiment, the plurality of flexible displacement portions are radiated from a center of the diaphragm portion. With this arrangement, the diaphragm is supported in a manner in which it can be vibrated satisfactorily.

According to an eighth embodiment, in the vibration sensor according to the seventh embodiment, the diaphragm has opening portions formed between it and the plurality of flexible displacement portions. With this arrangement, the diaphragm can be satisfactorily vibrated by vibrations and thereby vibrations can be detected satisfactorily.

According to a ninth embodiment, in the vibration sensor according to the eighth embodiment, the opening portions are disposed along a circumferential direction of the diaphragm portion. With this arrangement, vibrations can be detected more satisfactorily.

According to a tenth embodiment, in the vibration sensor according to the sixth embodiment, the holding means accommodates therein the substrate and the diaphragm in substantially closed state and holds the substrate and the supporting portion of the diaphragm. With this arrangement, the inside of the sensor can be prevented from being smudged by dusts or the like. Moreover, the diaphragm can be prevented from being vibrated by a sound pressure based on sounds applied to the vibration sensor. Therefore, vibrations can be detected satisfactorily.

According to an eleventh embodiment, a vibration sensor comprises a substrate, a plate-like diaphragm including a diaphragm portion, a supporting portion for supporting the diaphragm portion such that the diaphragm portion becomes able to move in parallel to the substrate and an opening portion formed between the diaphragm portion and the supporting portion, the plate-like diaphragm being opposed to the substrate with a predetermined interval and being opposed in parallel to the substrate, an electret film disposed either on the substrate at its surface opposing the diaphragm or on the diaphragm at its surface opposed to the substrate and holding means for holding the substrate and holding the supporting portion of the diaphragm in such a manner that the diaphragm portion comes close to or away from the substrate in parallel. With this arrangement, the diaphragm is vibrated by vibrations applied to the vibration sensor and thereby vibrations applied to the vibration sensor can be detected.

According to a twelfth embodiment, in the vibration sensor according to the eleventh embodiment, the opening portion is disposed along a circumferential direction of the diaphragm. With this arrangement, vibrations can be detected satisfactorily.

According to a thirteenth embodiment, in the vibration sensor according to the eleventh embodiment, the holding means is a housing for accommodating therein the substrate and the diaphragm in substantially closed state and holding the substrate and the supporting portion of the diaphragm. With this arrangement, the inside of the sensor can be prevented from being smudged by dusts or the like. Moreover, the diaphragm can be prevented from being vibrated by a sound pressure based on sounds applied to the vibration sensor and thereby vibrations can be detected satisfactorily.

According to a fourteenth embodiment, a navigation apparatus comprises position detecting means for detecting a current position of a navigation object, a vibration sensor comprising a plate-like diaphragm composed of a substrate, a diaphragm portion, a supporting portion, and a plurality of flexible displacement portions for coupling the diaphragm portion and the supporting portion such that the diaphragm portion and the supporting portion become able to move in parallel to the substrate, the plate-like diaphragm being opposed to the substrate with a predetermined interval and being placed in parallel to the substrate, an electret film being disposed either on the substrate at its surface opposing the diaphragm or on the diaphragm at its surface opposing the substrate, and holding means for holding the supporting portion of the diaphragm in such a manner that the diaphragm comes close to or away from the substrate in parallel, reproducing means for reading and reproducing map data, display means for displaying thereon the map data supplied thereto from the reproducing means, and control means for controlling an operation of the reproducing means based on an output signal from the vibration sensor and/or an output signal from the position detecting means. With this arrangement, a vibrated state of the position at which the navigation apparatus is installed can be detected based on the detected output of the vibrations sensor. Therefore, an operation of the navigation apparatus can be controlled satisfactorily.

According to a fifteenth embodiment, a navigation apparatus comprises position detecting means for detecting a current position of a navigation object, a vibration sensor comprising a plate-like diaphragm composed of a substrate, a diaphragm portion, a supporting portion for supporting the diaphragm portion such that the diaphragm portion becomes able to move in parallel to the substrate and an opposing portion disposed between the diaphragm portion and the supporting portion, the plate-like diaphragm being opposed to the substrate with a predetermined interval and being placed in parallel to the substrate, an electret film being disposed either on the substrate at its surface opposing the diaphragm or on the diaphragm at its surface opposing the substrate, and holding means for holding the substrate and holding the supporting portion of the diaphragm in such a manner that the diaphragm portion comes close to or away from the substrate in parallel, reproducing means for reading and reproducing map data, display means for displaying thereon the map data supplied thereto from the reproducing mean, and control means for controlling an operation of the reproducing means based on an output signal from the vibration sensor and/or an output from the position detecting means. With this arrangement, the vibrated state of the position at which the navigation apparatus is installed can be detected based on the detected output of the vibration sensor. Therefore, an operation of the navigation apparatus can be controlled satisfactorily.

BEST MODE FOR CARRYING OUT THE INVENTION

A vibration sensor according to the present invention will hereinafter be described in detail with reference to the drawings.

Figure 5:
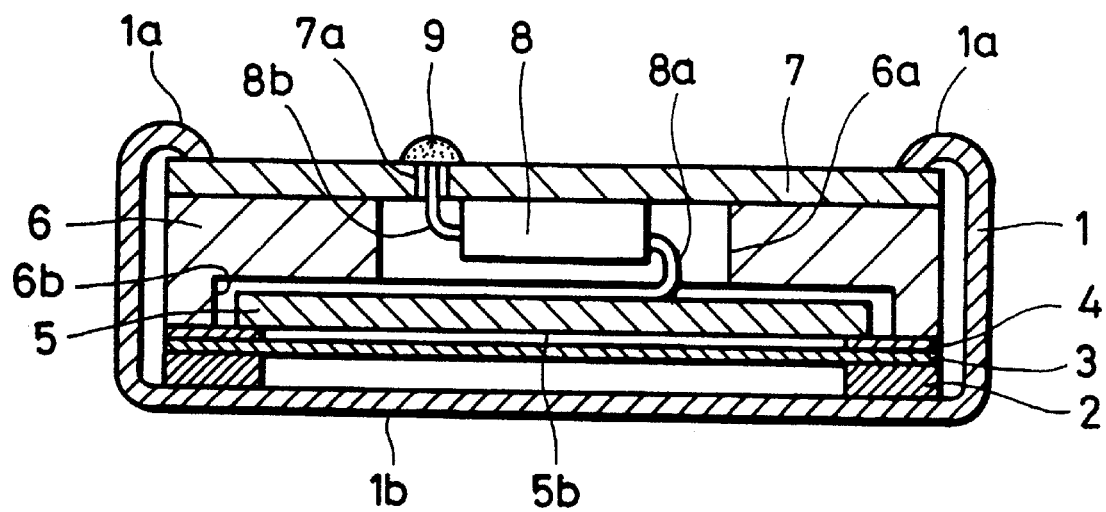
FIG. 5 is a cross-sectional view illustrating a vibration sensor according to an embodiment of the present invention.

FIG. 5 shows in cross-sectional form a vibration sensor according to the invention. A case 1 is a cylindrically-shaped case made of a material such as aluminum Al. One end of the case is closed to form a bottom portion 1b and the other end is opened. The case 1 houses therein assembly elements shown in FIG. 6. A diaphragm ring 2 is disposed between a diaphragm, which will be described later on, and the bottom portion 1b of the case 1 are annularly-shaped by use of synthetic resin material or the like. The diaphragm ring 2 has an opening portion 2a of substantially the same size as an inner diameter of a supporting portion of the diaphragm which will be described later on.

Figure 6:
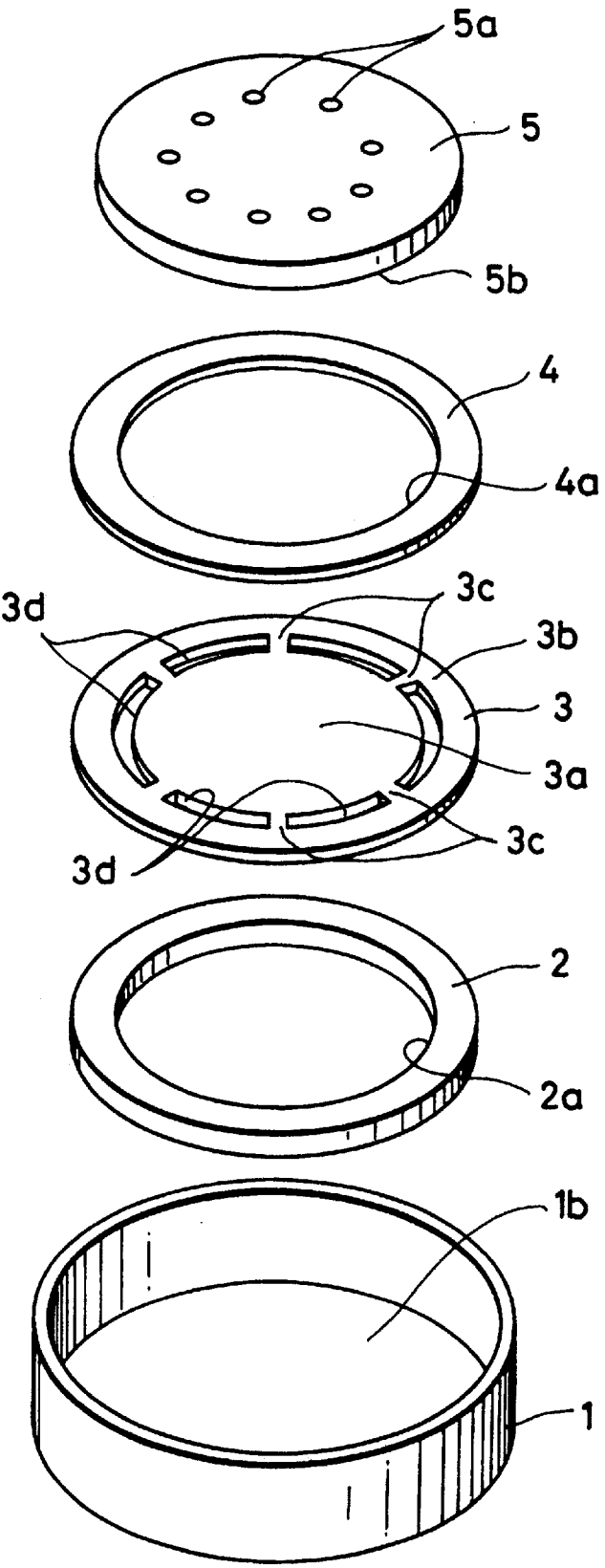
FIG. 6 is an exploded perspective view illustrating a main portion of the vibration sensor according to the embodiment in exploded form.
Figure 7:
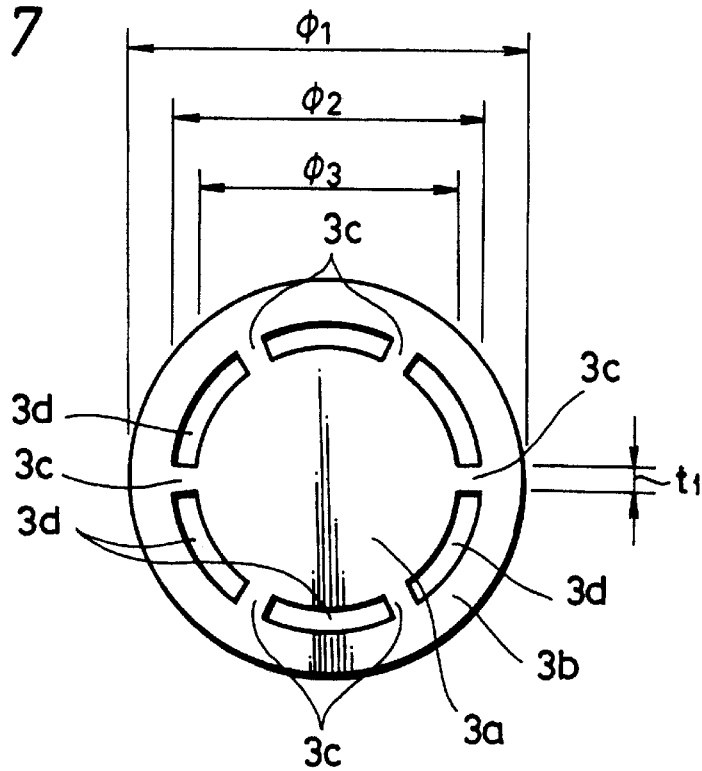
FIG. 7 is a plan view showing a diaphragm of the vibration sensor according to the embodiment.

A diaphragm 3 is composed of a diaphragm portion 3a, a supporting portion 3b, a plurality of flexible displacement portions 3c and a plurality of opening portions 3d as shown in FIG. 6. The diaphragm is a disk-shaped diaphragm made of a metal material such as stainless steel. By way of example, as shown in FIG. 7, the diaphragm 3 is formed of 40 $\mu$m-thick stainless steel such that an outer diameter $\phi_1$ of the whole diaphragm is about 9 mm, an inner diameter $\phi_2$ of the supporting portion 3b is about 7 mm, an outer diameter $\phi_3$ of the diaphragm 3a is about 6 mm and a width of the flexible displacement portion 3c is about 2 mm. The plurality of flexible displacement portions 3c are narrow and radiated from the center of the diaphragm 3a at equal intervals. According to this embodiment, although there are six flexible displacement portions 3c between the diaphragm portion 3a and the supporting portion 3b as shown in FIG. 6, the number of the flexible displacement portions 3c is not limited thereto and at least more than three flexible displacement portions 3c may be sufficient for enabling the diaphragm portion 3a to be displaced or moved in parallel to a back plate which will be described later on. A plurality of opening portions 3d are disposed between the flexible displacement portions 3c at equal intervals in the diaphragm portion 3a and the supporting portion 3b such that long axes thereof are extended along the circumferential direction of the diaphragm portion 3a. These opening portions 3d are disposed in order to prevent the diaphragm 3 from being vibrated by a sound pressure based on sounds applied to the vibration sensor from the outside. If a plurality of opening portions are provided along the circumferential direction of the diaphragm portion 3a as shown in FIG. 7, then the area in which the diaphragm portion 3a and the electret film oppose to each other can be prevented from being reduced unlike the aforesaid vibration sensor having the diaphragm with the through-hole defined at its central portion. As a consequence, the vibration sensor can be prevented from detecting sounds from the outside and therefore the detection sensitivity of the vibration sensor can be prevented from being lowered. The diaphragm 3 has an epoxy resin insulating layer having a thickness of about 1 $\mu$m on its surface opposing the back plate which will be described later. According to this embodiment, since the diaphragm 3 detects vibrations generated between it and the monitored object, the diaphragm is made of a material having a relatively large mass, e.g., material of metal such as stainless steel.

A spacer 4 is a ring-shaped spacer made of a film-shaped synthetic resin having a thickness of about 40 $\mu$m. The spacer 4 includes an opening portion 4a as shown in FIG. 6.

The opening portion 4a is as large as about the inner diameter of the supporting portion 3b of the diaphragm similarly to the opening portion 2a of the diaphragm ring 2. A back plate 5 is opposed to the diaphragm 3 through the spacer 4. The back plate 5 is formed of a circular metal plate having a diameter larger than that of the diaphragm portion 3a of the diaphragm 3. The back plate 5 has an electret film 5b on its surface opposing the diaphragm 3 and also has a plurality of holes 5a.

A cylindrical frame 6 with an opening portion 6a formed at its central portion made of a synthetic resin material is attached to the peripheral portion of the back plate 5. The frame 6 has formed on its one end a recess portion 6b large enough to surround the back plate 5. The bottom surface of the recess portion 6b is communicated with the opening portion 6a. The opening portion 6a accommodates therein a field-effect transistor (FET) 8 wherein one terminal 8b is connected, through an opening 7a in the circuit substrate 7, to a the circuit substrate 7 as a terminal board by a solder 9. Another terminal 8a of the FET 8, i.e., gate is connected to the diaphragm 3 of the back plate 5 on its surface opposite to the opposing surface of the diaphragm 3. The FET 8 is used to detect how much a capacity of electric charges accumulated between the diaphragm 3 and the back plate 5 is changed when the diaphragm 3 is vibrated or displaced relative to the back plate 5. The other end 1a of the case 1 is caulked to press the circuit substrate 7 down and the case a is almost closed under the condition that the case 1 accommodates the respective assembly elements. Since the case 1 is almost closed, the inside of the case 1 can be prevented from being smudged by dust or the like. Moreover, the case 1 is placed in the closed state enough for preventing the diaphragm 3 from being vibrated by a sound pressure based on sounds applied to the vibration sensor.

The supporting portion 3b of the diaphragm 3 is held by the frame 6 through the diaphragm ring 2 and the spacer 4. As a consequence, the diaphragm portion 3 is supported by a plurality of flexible displacement portions 3c in parallel to the back plate 5 such that it can be displaced or vibrated. If a plurality of opening portions 3d are formed on the diaphragm 3, then it is possible to prevent the diaphragm 3 from being vibrated by a sound pressure based on sounds applied to the vibration sensor. Since the diaphragm 3 has almost no electric charges accumulated at its portion adjacent to the supporting portion 3b and such adjacent portion is hardly vibrated as compared with the diaphragm portion 3a, a vibration detection sensitivity can be prevented from being degraded by the opening portion 3d formed at the portion wherein the diaphragm portion 3a and the supporting portion 3b are joined.

In the above vibration sensor, the diaphragm 3 and the back plate 5 have therebetween accumulated electric charges of capacity corresponding to a size of a clearance provided between the diaphragm 3 and the back plate 5. When the diaphragm 3 is vibrated relative to the back plate, the clearance between the diaphragm 3 and the back plate 5 is changed, thereby changing the capacity of electric charges accumulated between the diaphragm 3 and the back plate 5. When the FET 8 detects the change of capacity, the vibration sensor generates an electrical signal corresponding to the vibrations of the diaphragm. Thus, it is possible to obtain the output signal serving as a detected result of vibration.

Figure 1:
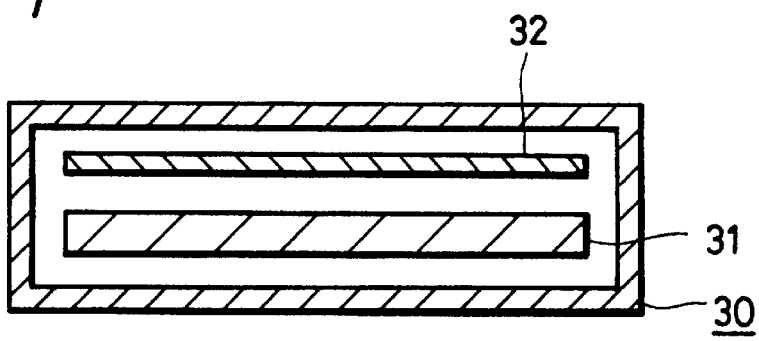
FIG. 1 is a cross-sectional view illustrative of a principle of a vibration sensor.
Figure 2:
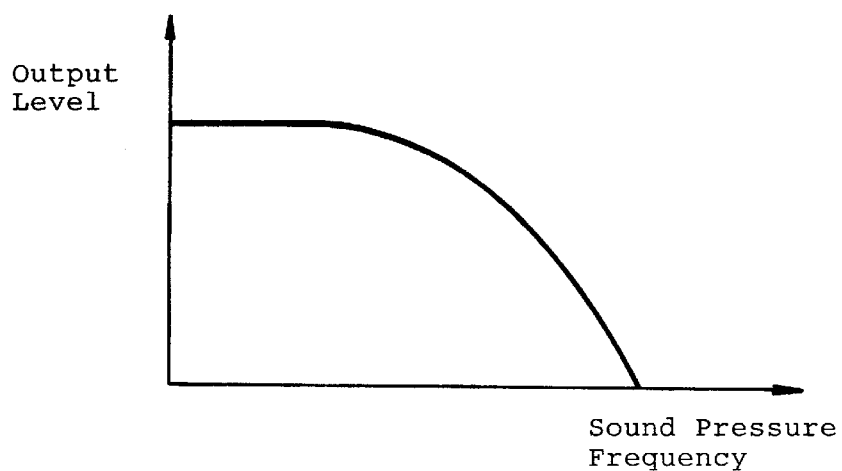
FIG. 2 is a sound pressure frequency characteristic graph of a closed-type vibration sensor.
Figure 3:
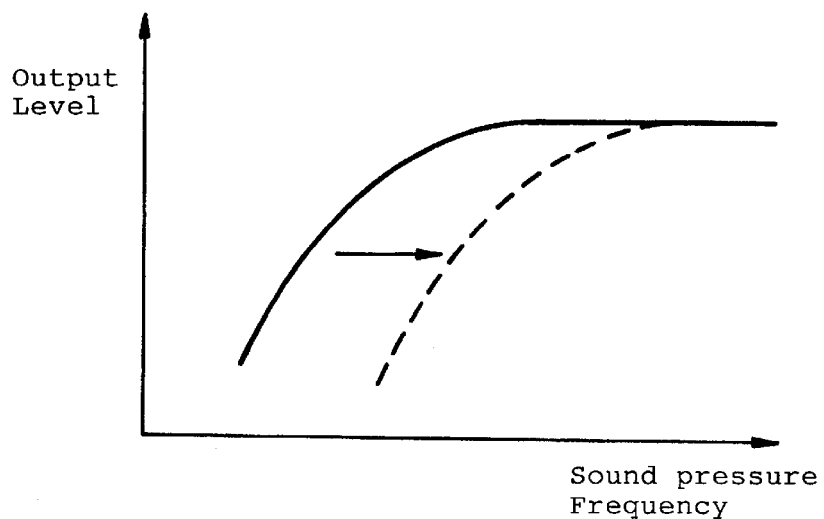
FIG. 3 is a frequency characteristic graph showing a sound pressure response of a diaphragm with a through-hole defined therein.
Figure 4:
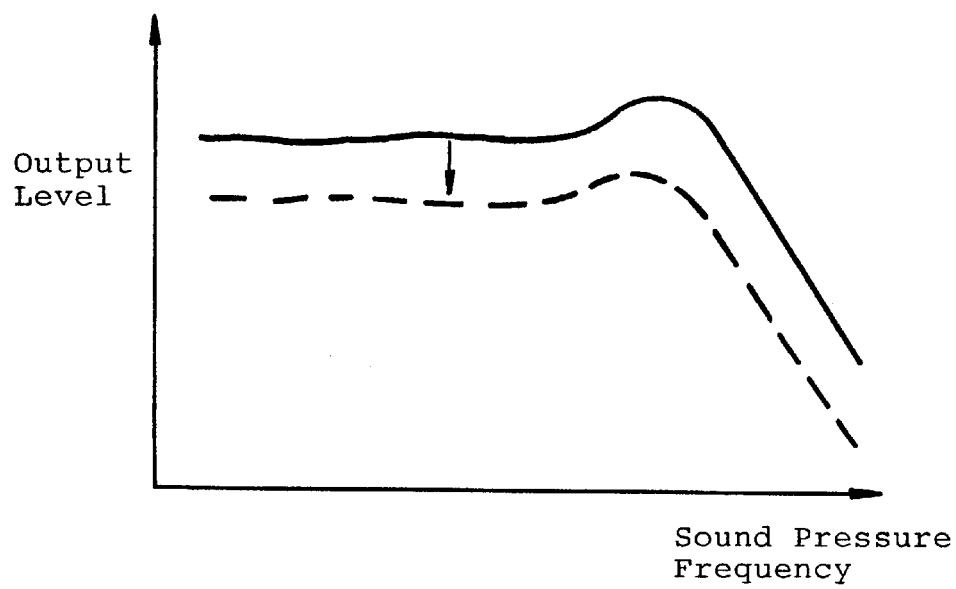
FIG. 4 is a frequency characteristic graph showing a vibration response of a diaphragm with a through-hole defined therein.

If the diaphragm of the vibration sensor is fixed as in the vibration sensor shown in FIG. 1, when the vibration sensor and the monitored object with the vibration sensor attached thereto, e.g., a vehicle, are vibrated, the vibration sensor is vibrated with vibrations. In other words, because the back plate 5 of the vibration sensor is vibrated relative to the diaphragm 3, the capacity of electric charges accumulated between the diaphragm 3 and the back plate 5 is changed. The vibration sensor can obtain the output signal corresponding to vibrations by detecting the change of capacity with the FET 8. Conversely, since considering the state that the vibration sensor is fixed together with the detected object, if a vibration is applied to the vibration sensor, the diaphragm 3 is vibrated relative to the back plate 5, thereby changing the capacity of electric charges accumulated between the diaphragm 3 and the back plate 5. The vibration sensor can output the output signal corresponding to the vibration by detecting the change of the capacity with the FET B. In that case, even when sounds are applied to the vibration sensor from the outside, a plurality of opening portions 3d disposed on the diaphragm 3 can prevent the diaphragm 3 from being vibrated. Therefore, the vibration sensor can satisfactorily detect only vibrations applied to the vibration sensor.

Figure 8:
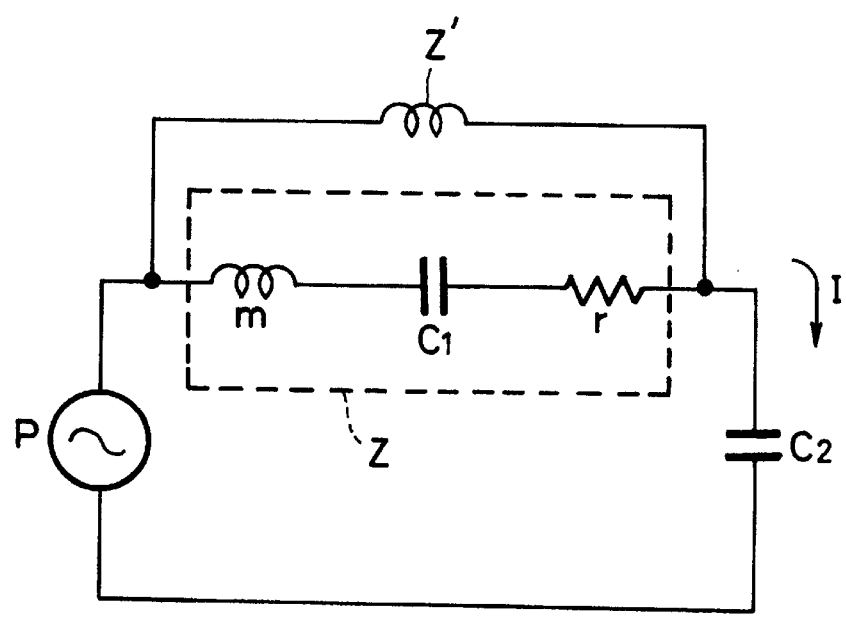
FIG. 8 is a circuit diagram showing an equivalent circuit of the vibration sensor according to the embodiment.

FIG. 8 shows an equivalent circuit of the vibration sensor according to this embodiment. The diaphragm portion 3a of the diaphragm 3 shown by m, $c_1$, r generates an equivalent impedance for a sound pressure P. Since the diaphragm 3 has the opening portions 3d defined therein, an impedance z' based on the opening portions 3d is connected to the impedance of the diaphragm portion 3a in parallel. I assumes a speed of the vibration unit 3 of the diaphragm 3. Then, a displacement x of the diaphragm portion 3a of the diaphragm 3 is expressed by the following equation:

$$x = I/(j\omega) = P \bigg/ \left( \frac{z \cdot z'}{z + z'} \cdot j\omega \right)$$

As described before, when the distance between the diaphragm 3 and the back plate is changed, the electrostatic capacity of the capacitor composed of the diaphragm 3 and the back plate 5 is changed. As a consequence, the displacement of the diaphragm 3 is detected as the change of the electrostatic capacity. Therefore, the output signal from the vibration sensor is proportional to the displacement x of the diaphragm portion of the diaphragm 3.

Figure 9:
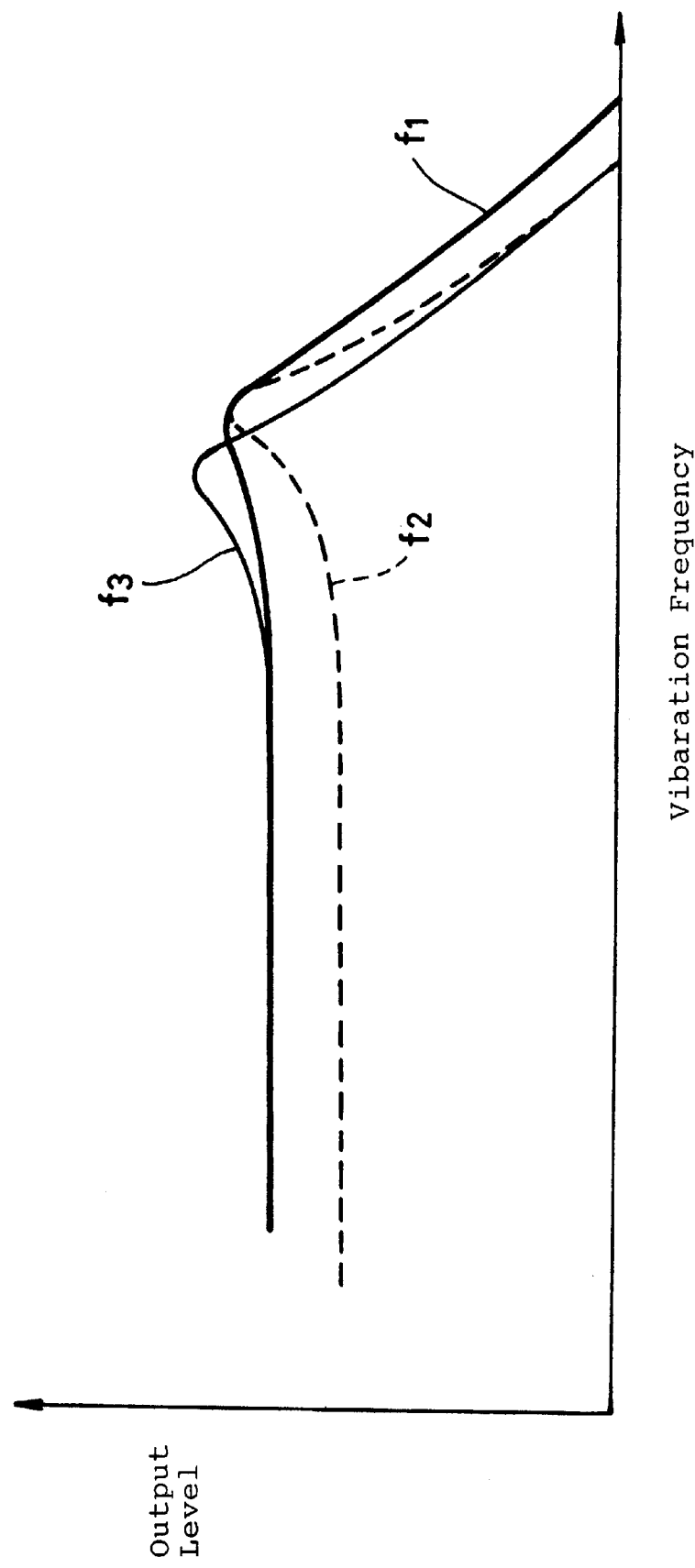
FIG. 9 is a frequency characteristic graph of the vibration sensor according to the embodiment.

FIG. 9 shows a frequency characteristic of the vibration sensor according to this invention. A characteristic denoted by $f_1$ shows a frequency characteristic of the vibration sensor according to this invention. Since the vibration sensor according to this invention is of the type that the diaphragm portion 3a and the supporting portion 3c of the diaphragm 3 are coupled by a plurality of flexible displacement portions 3e, a compliance of the diaphragm 3 can be raised. When the compliance of the diaphragm 3 is raised, this is equivalent to the fact that the edge supporting a diaphragm of an ordinary speaker is softened. In the diaphragm 3 according to this embodiment, the diaphragm portion 3a and the supporting portion 3b are coupled by a plurality of flexible displacement portions with small widths so that the diaphragm portion 3a can be easily vibrated. Therefore, when the compliance of the diaphragm is raised, this can achieve substantially similar effects that the speaker edge is softened. As a result, according to the vibration sensor according to the present invention, the output level thereof can be raised higher than the frequency characteristic $f_2$ of the conventional vibration sensor. The characteristic of high band portion can be improved as compared with a frequency characteristic $f_3$ of the vibration sensor having substantially the same output level of this embodiment. A weight of the diaphragm of the vibration sensor according to this embodiment can be reduced with the result that the peak portion of the high band portion of the frequency can be shifted to a higher frequency. Also, the level of the peak portion can be lowered.

A navigation apparatus using the vibration sensor according to the embodiment of the present invention will be described with reference to FIG. 10. The navigation apparatus shown in FIG. 10 is for use as an automobile navigation apparatus.

Figure 10:
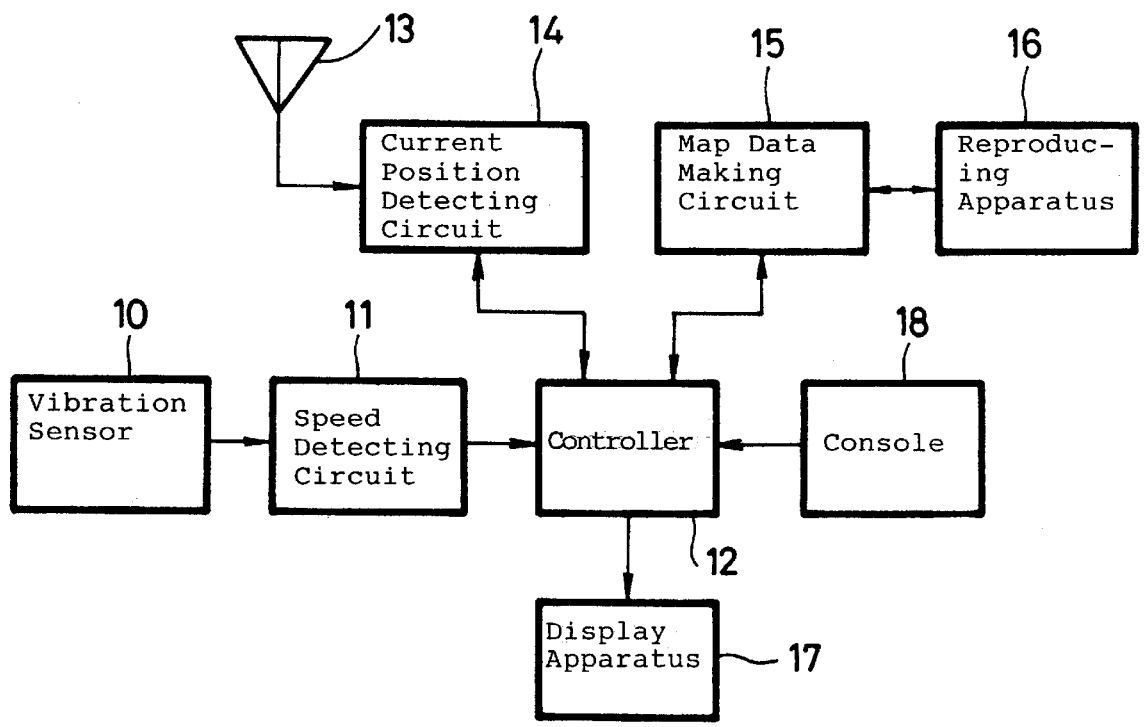
FIG. 10 is a block diagram showing a navigation apparatus to which there is applied the vibration sensor according to the embodiment.

In FIG. 10, the navigation apparatus comprises a vibration sensor 10, a speed detecting circuit 11, a controller 12, an antenna 13, a current position detecting circuit 14, a map data making circuit 15, a reproducing apparatus 16, a display apparatus 17 and a console 18.

The vibration sensor 10 is the vibration sensor shown in FIGS. 5 and 6. The vibration sensor 10 detects an acceleration of the vehicle. An output signal indicative of an acceleration from the vibration sensor 10 is supplied to the speed detecting circuit 11. The speed detecting circuit 11 supplies an output signal indicative of a current speed of vehicle being used as a mobile object by integrating the output signal supplied thereto from the vibration sensor 10.

On the other hand, the controller 12 is supplied with an output signal from the current position detecting circuit 14. The current position detecting circuit 14 measures the current position of the vehicle based on a signal received at the antenna 13 from a position measuring satellite, and supplies data concerning the current position to the controller 12. When the position of the vehicle is measured by the satellite, a GPS (Global Positioning System) is used. The controller 12 controls operation of the map data making circuit 15 based on data supplied thereto from the current position detecting circuit 15 and/or the speed detecting circuit 11 to thereby make map data to be displayed on the display apparatus 17.

The map data making circuit 15 reproduces data corresponding to data concerning the vehicle current position obtained by the calculation from the current position detecting circuit 14 from a CD-ROM by supplying a control signal to the reproducing apparatus which reproduces the CD-ROM serving as a recording medium with map data recorded therein and generates map data based on data thus read out. The reproducing apparatus 16 includes a optical head for reading data recorded on the CD-ROM, a rotation drive mechanism for rotating the disk and a signal processing circuit for effecting a signal processing such as error-correction on the data read out from the disk.

The display apparatus 17 is composed of liquid-crystal display device or the like. The display apparatus displays map information based on the map data made by the map data making circuit 15. The console 18 is composed of a plurality of operation keys. When the keys on the console are operated, various operation mode setting or switching data, such as data for accessing map displayed on the display apparatus 17 or data for switching display modes are supplied to the controller 12.

In the navigation apparatus, the current position detecting circuit 14 detects data concerning the automobile's current position by calculation based on the signal received at the antenna 13 from the satellite. The current position data thus obtained is supplied to the controller 12. under control of the controller 12, the reproducing apparatus reproduces data from the CD-ROM corresponding to the current position data supplied from the current position detecting circuit 14 and supplies read out data to the map data making circuit 15, which is converted to map data and displayed on the display apparatus 17 through the controller 12. When it is detected on the basis of the output from the velocity sensor 10 that the automobile is not stopped or it is detected on the basis of the output from the speed detecting circuit 11 that the automobile is running at a speed higher than a predetermined speed, the controller 12 is disabled to receive input data (all operation input data or only relatively complicated operation input data) from the console 18 or such data are made invalid. Accordingly, under the condition that the automobile is running, the driver cannot switch the operation mode of the navigation apparatus or switch map information displayed on the display apparatus 17 by the console 18. Therefore, it is possible to prevent an accident from being caused when the driver switches the operation mode of the navigation apparatus or map information during driving. Further, if the vibration sensor shown in FIGS. 5 and 6 is used as the vibration sensor 10, then it is possible to prevent the navigation apparatus from malfunctioning under control of the controller 12 as a result of the vibration sensor detecting sounds generated in the automobile compartment, such as conversations of passengers or sounds generated in the outside of the vehicle.

Figure 11:
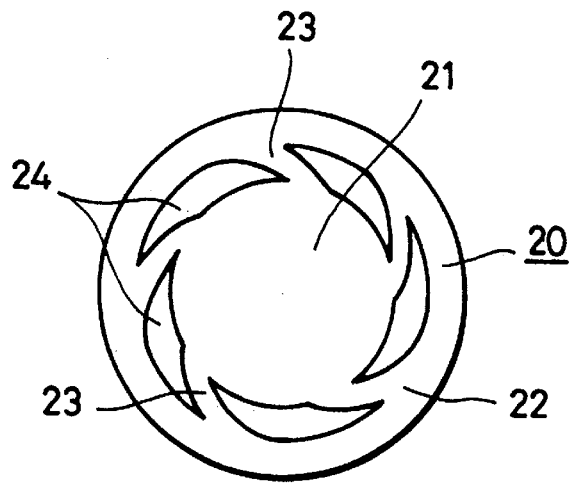
FIG. 11 is a plan view showing a modified example of a vibration sensor.

While the diaphragm portion 3a and the supporting portion 3b of the diaphragm 3 are coupled by a plurality of flexible displacement portions 3c each radiated from the center of the diaphragm portion 3a in straight-line as described above, the above shape may be modified as shown in FIG. 11. FIG. 11 shows a modified example of the diaphragm 3. A diaphragm 20 shown in FIG. 11 includes a disk-like diaphragm portion 21, a supporting portion 22, a plurality of flexible displacement portions 23 and a plurality of opening portions. These elements are integrally formed as an integrated disk by use of a material such as a metal material or the like. A plurality of flexible displacement portions 23 are extended at an equal interval along the tangential line of the disk-like diaphragm portion 21. A plurality of opening portions 24 are formed along the circumferential direction of the diaphragm portion 21 among the diaphragm portion 21, the supporting portion 22 and a plurality of flexible displacement portions 23 at equal intervals.

In the case of the diaphragm 20 shown in FIG. 11, similarly to the diaphragm 3 shown in FIG. 7, since the opening portion 24 is formed without reducing the area of the portion opposing the electret film 5b, i.e., the area of the diaphragm portion 21, a vibration detection sensitivity can be prevented from being degraded. Further, since the diaphragm 20 can be prevented from being vibrated with sounds applied to the vibration sensor, the vibration sensor can satisfactorily detect vibrations.

As set forth above, since the supporting portion of the diaphragm of the vibration sensor and the diaphragm portion are coupled by a plurality of flexible displacement portions disposed such that the diaphragm portion becomes able to move in parallel to the back plate, the vibration sensor can satisfactorily detect vibrations without lowering a sensitivity at which vibrations are detected and without vibrating the diaphragm by sound pressure applied to the vibration sensor.

The vibration sensor according to the present invention can be modified variously without departing from the gist of the present invention.

While the electret film, for example, is disposed on the back plate in the vibration sensor, the present invention is not limited thereto and the electret film may be disposed on the diaphragm at its surface opposing the back plate.

Further, while the vibration sensor is of the type using the FET to detect how much the capacity of electric charges are changed with the change of clearance provided between the diaphragm and the back plate as described above, the present invention is not limited thereto and the present invention can be applied to a vibration sensor of the type using a capacitor formed between a diaphragm and a substrate serving a back electrode so as to apply a bias voltage to the portion between the diaphragm and the back electrode.

Incidentally, it is needless to say that the vibration sensor according to the present invention is not limited to the navigation apparatus and can be applied to a wide variety of apparatus.

We claim:

1. A vibration sensor comprising:

a substrate;

a disk-shaped diaphragm from which are integrally formed a diaphragm portion, a supporting portion and a plurality of flexible displacement portions, wherein said displacement portions extend radially at equal intervals around a circumference of said diaphragm portion between said diaphragm portion and said supporting portion such that said diaphragm portion is able to move relative to said substrate, said diaphragm being spaced from said substrate by a predetermined interval to form a capacitor; and holding means for holding said substrate and holding said supporting portion of said diaphragm spaced at said predetermined interval, wherein a vibration creates a change of electrostatic capacitance between said diaphragm and said substrate;

wherein said holding means is a housing for accommodating therein said substrate and said diaphragm and holding said substrate and said supporting portion of said diaphragm; and wherein said holding means comprises a diaphragm ring, a spacer element and a cylindrical frame.

2. A vibration sensor according to claim 1, wherein said diaphragm includes, between said plurality of flexible displacement portions, means for canceling a sound pressure applied to said vibration sensor.

3. A vibration sensor according to claim 2, wherein said means for canceling a sound pressure comprises a plurality of opening portions disposed at equal intervals around said circumference of said diaphragm portion and disposed respectively between adjacent flexible displacement portions.

4. A vibration sensor according to claim 1, wherein said disk-shaped diaphragm is made of a metal material.

5. A vibration sensor according to claim 4, wherein said metal material is 40 $\mu$m-thick stainless steel.

6. A vibration sensor according to claim 1, wherein said spacer element is made of a film-shaped synthetic resin having a thickness of about 40 $\mu$m.

7. A vibration sensor according to claim 1, wherein an FET within said sensor is used to detect the change of electrostatic capacity formed between said diaphragm and said substrate.

8. A vibration sensor according to claim 1, wherein said flexible displacement portions are disposed at an angle to a radial direction of said diaphragm portion.

9. A vibration sensor according to claim 1, wherein a distance between said diaphragm portion and said supporting portion is less than a length of said flexible displacement portions.

* * * * *